US008288094B2

(12) United States Patent
Wain-Hobson et al.

(10) Patent No.: US 8,288,094 B2
(45) Date of Patent: Oct. 16, 2012

(54) APOBEC3 MEDIATED DNA EDITING

(75) Inventors: Simon Wain-Hobson, Montigny le Bretonneux (FR); Jean-Pierre Vartanian, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 12/100,212

(22) Filed: Apr. 9, 2008

(65) Prior Publication Data

US 2009/0260090 A1  Oct. 15, 2009

(51) Int. Cl.
C12Q 1/68 (2006.01)

(52) U.S. Cl. ....... 435/6.1; 435/6.11; 435/6.12; 435/6.13

(58) Field of Classification Search .................... 435/6.1
See application file for complete search history.

(56) References Cited

U.S. PATENT DOCUMENTS

| 4,736,866 A | 4/1988 | Leder et al. |
| 4,870,009 A | 9/1989 | Evans et al. |
| 4,873,191 A | 10/1989 | Wagner et al. |
| 4,946,778 A | 8/1990 | Ladner et al. |

FOREIGN PATENT DOCUMENTS

| WO | 90/11364 | 10/1990 |
| WO | 97/07668 | 3/1997 |
| WO | 97/07669 | 3/1997 |
| WO | 2007/091125 | 8/2007 |

OTHER PUBLICATIONS

Chiba et al, J Mol Med, 2009, 87:1023-1027.*
Cascalso, M, Jour Immunol, 2004, 172:6513-6518.*
Xu et al 2007, Hepatology, 46:1810-1820.*
Smith, 2011—In Press, Seminars in Developmental Biology, pp. 1-11.*
Arbyn et al. "Review of Current Knowledge on HPV Vaccination: An Appendix to the European Guidelines for Quality Assurance in Cervical Cancer Screening." Journal of Clinical Virology 38: 189-197 (2007).
Bishop et al. "Cytidine Deamination of Retroviral DNA by Diverse APOBEC Proteins." Current Biology 14: 1392-1396 (Aug. 10, 2004).
Bogerd et al. "Cellular Inhibitors of Long Interspersed Element 1 and Alu Retrotransposition." PNAS 103(23): 8780-8785 (Jun. 6, 2006).
Bronstein et al. "Chemiluminescent Reporter Gene Assays: Sensitive Detection of the GUS and SEAP Gene Products." Biotechniques 17(1): 172-177 (1994).
Butler, "The Amplified ELISA: Principles of and Applications for the Comparative Quantitation of Class and Subclass Antibodies and the Distribution of Antibodies and Antigens in Biochemical Separates." Methods in Enzymology 73: 482-523 (1981).
Cogliano et al. "Carcinogenicity of Human Papillomaviruses." Lancet Oncology 6: 204 (Apr. 2005).
Conticello et al. "Evolution of the AID/APOBEC Family of Polynucleotide (Deoxy)Cytidine Deaminases." Molecular Biology and Evolution 22(2): 367-377 (2005).
Dang et al. "Identification of APOBEC3DE as Another Antiretroviral Factor from the Human APOBEC Family." Journal of Virology 80(21): 10522-10533 (Nov. 2006).
de Villiers et al. "Classification of Papillomaviruses." Virology 324: 17-27 (2004).
di Noia et al. "Molecular Mechanisms of Antibody Somatic Hypermutation." Annu. Rev. Biochem. 76: 1-22 (2007).
Goodman et al. "AID-Initiated Purposeful Mutations in Immunoglobulin Genes." Advances in Immunology 94: 127-155 (2007).
Greenman et al. "Patterns of Somatic Mutation in Human Cancer Genomes." Nature 446(8): 153-158 (2007).
Guatelli et al. "Isothermal, in vitro Amplification of Nucleic Acides by a Multienzyme Reaction Modeled After Retoviral Replication." PNAS 87: 1874-1878 (Mar. 1990).
Harris et al. "DNA Deamination Mediates Innate Immunity to Retr5oviral Infection." Cell 113: 803-809 (Jun. 13, 2003).
Helene, "The Anti-Gene Strategy: Control of Gene Expression by Triplex-Forming-Oligonucleotides." Anti-Cancer Drug Design 6: 569-584 (1991).
Houghten et al. "Generation and Use of Synthetic Peptide Combinatorial Libraries for Basic Research and Drug Discovery." Nature 354: 84-86 (Nov. 7, 1991).
Huse et al. "Generation of a Large Combinatorial Library of the Immunoglobulin Repertoire in Phage Lambda." Science 246: 1275-1281 (Dec. 8, 1989).
Jarmuz et al. "An Anthropoid-Specific Locus of Orphan C to U RNA-Editing Enzymes on Chromosome 22." Genomics 79(3): 285-296 (Mar. 2002).
Kinomoto et al., "All APOBEC3 Family Proteins Differentially Inhibit Line-1 Retrotrasposition." Nucleic Acids Research 35:9, pp. 2955-2964, 2007.
Kwoh et al. "Transcription-Based Amplification System and Detection of Amplified Human Immunodeficiency Virus Type 1 with a Bead-Based Sandwich Hybridization Format." PNAS 86: 1173-1177 (Feb. 1989).

(Continued)

Primary Examiner — Valarie Bertoglio
(74) Attorney, Agent, or Firm — Kenyon & Kenyon LLP

(57) ABSTRACT

The present invention relates to methods and compositions for preventing the occurrence or progression of a cancer or pre-cancerous condition associated with expression, or overexpression of human cytidine deaminases of the APOBEC3 family. The invention also relates to drug screening assays designed to identify compounds that regulate the activity, or level of expression, of hA3A, hA3C and hA3H. The invention further relates to transgenic mice, as well as cells derived from said mice, that have been genetically engineered to express, or over-express hA3A, hA3C and/or hA3H. Such mice may be utilized to screen for, or identify, compounds that modulate the activity, or expression, of the human cytidine deaminases. The present invention also provides topical compositions such as cosmetic lotion, crème, or sunscreen for use on the skin, which comprise one or more inhibitors of human cytidine deaminase activity. The present invention relates to a double stranded DNA obtained following opening up of its duplex structure, said DNA being edited with cellular protein normally or abnormally expressed in the nucleus of an eukaryotic cell. The mono stranded DNA derived from the said double stranded DNA is a part of the present invention.

4 Claims, 2 Drawing Sheets

OTHER PUBLICATIONS

Figure 1:
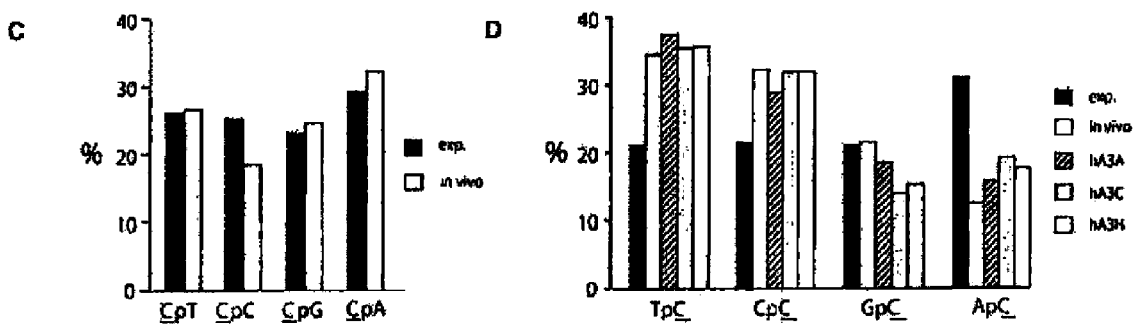

Lam et al. "A New Type of Synthetic Peptide Library for Identifying Ligand-Binding Activity." Nature 354: 82-84 (Nov. 7, 1991).

Lecossier et al. "Hypermutation of HIV-1 DNA in the Absence of the Vif Protein." Science 300: 1112 (May 16, 2003).

Lizardi et al. "Exponential Amplification of Recombinant-RNA Hybridization Probes." Bio/Technology 6: 1197-1202 (Oct. 1988).

Madsen et al. "Psoriasis Upregulated Phorbolin-1 Shares Structural but not Functional Similarity to the mRNA-Editing Protein APOBEC-1." Journal of Investigative Dermatology 113: 162-169 (1999).

Maher, "DNA Triple-Helix Formation: An Approach to Artificial Gene Repressors?" Bioassays 14(12):807-815 (Dec. 1992).

Malek et al. "Nucleic Acid Sequence-Based Amplification (NASBA™)." Methods in Molecular Biology 28: 253-260 (1994).

Mangeat et al. "Broad Antiretroviral Defence by Human APOBEC3G Through Lethal Editing of Nascent Reverse Transcripts." Nature 424: 99-103 (Jul. 3, 2003).

Mariani et al. "Species-Specific Exclusion of APOBEC3G from HIV-1 Virons by Vif." Cell 114: 21-31 (2003).

Matsumoto et al. "Helicobacter Pylori Infection Triggers Aberrant Expression of Activation-Induced Cytidine Deaminase in Gastric Epithelium." Nature Medicine 13(4): 470-4766 (Apr. 2007).

OhAinle et al. "Adaptive Evolution and Antiviral Activity of the Conserved Mammalian Cytidine Deaminase APOBEC3H." Journal of Virology 80(8): 3853-3862 (Apr. 2006).

Okazaki, et al. "Role of AID in Tumorigenesis." Advances in Immunology 94: 245-273 (2007).

Pham et al. "Processive AID-Catalysed Cytosine Deamination on Single-Stranded DNA Simulates Somatic Hypermutation." Nature 424: 103-107 (Jul. 3, 2003).

Sarver et al. "Ribozymes as Potential Anti-HIV-1 Therapeutic Agents." Science 247: 1222-1225 (Mar. 9, 1990).

Sjoblom et al. "The Consensus Coding Sequences of Human Breast and Colorectal Cancers." Science 314: 268-274 (Oct. 13, 2006).

Songyang et al. "SH2 Domains Recognize Specific Phosphopeptide Sequences." Cell 72: 767-778 (Mar. 12, 1993).

Stunkel et al. "The Chromatin Structure of the Long Control Region of Human Papillomavirus Type 16 Represses Viral Oncoprotein Expression." Journal of Virology 73(3): 1918-1930 (1999).

Suspène et al. "APOBEC3G Is a Single-Stranded DNA Cytidine Deaminase and Functions Independently of HIV Reverse Transcriptase." Nucleic Acids Research 32(8): 2421-2429 (2004).

Suspène et al. "Recovery of APOBEC3-Edited Human Immunodeficiency Virus G->A Hypermutants by Differential DNA Denaturation PCR." Journal of General Virology 86: 125-129 (2005).

Suspène et al. "Extensive Editing of Both Hepatitis B Virus DNA Strands by APOBEC3 Cytidine Deaminases in vitro and in vivo." PNAS 102(23): 8321-8326 Jun. 7, 2005).

Trivedi, et al. "Gene Array Expression Profiling in Acne Lesions Reveals Marked Upregulation of Genes Involved in Inflammation and Matrix Remodeling." Journal of Investigative Dermatology 126: 1071-1079 (2006).

Voller, "The Enzyme Linked Immunosorbent Assay (ELISA)", 1978, Diagnostic Horizons 2:1-7, Microbiological Associates Quarterly Publication, Walkersville, Md.

Wiegand et al. "A Second Human Antiretroviral Factor, APOBEC3F, Is Suppressed by the HIV-1 and HIV-2 Vif Proteins." The EMBO Journal 23(12): 2451-2458 (2004).

Wilmut et al. "Viable Offspring Derived from Fetal and Adult Mammalian Cells." Nature 385: 810-813 (Feb. 27, 2007).

Wu et al. "Receptor-Mediated in Vitro Gene Transformation by a Soluble DNA Carrier System." The Journal of Biological Chemistry 262(10): 4429-4432 (Apr. 5, 1987).

Zhang et al. "The Cytidine Deaminase CEM15 Induces Hypermutation in Newly Synthesized HIV-1 DNA." Nature 424: 94-98 (Jul. 3, 2003).

* cited by examiner

SEQUENCE LISTING

```
<160> NUMBER OF SEQ ID NOS: 30

<210> SEQ ID NO 1
<211> LENGTH: 28
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 1
tattaacacc gcacccgttg trrctaat                                            28

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catcaatata tgggatacag aggyttt                                             27

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttaaaagact acacctacar ratgtatt                                            28

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgcagagtc ttacctgtgt attttat                                             27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgcttgccaa ccattccatt gtttttt                                             27

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttgcttgcag tacacacatt ctaatatt                                            28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtacattgtg tcatataaaa taaatca        27

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgggtcct gaaacattgc agttctcttt t        31

<210> SEQ ID NO 9
<211> LENGTH: 120
<212> TYPE: DNA
<213> ORGANISM: Human papillomavirus

<400> SEQUENCE: 9
gtcttcattg tttatggttt accgcgctcc aaagacggtt tgcccaaaga cggtttgcca        60
accgcggtta ggacttgttt caatttgctg ccaaacttat ctggtcgtgc tccaacgggt        120

<210> SEQ ID NO 10
<211> LENGTH: 120
<212> TYPE: DNA
<213> ORGANISM: Human papillomavirus

<400> SEQUENCE: 10
gtcttcattg tttatggttt accgcgctcc aaaaacggtt tgcccaaaaa cagtttgcca        60
accgcagtta aaacttactt caatttgctg ccaaacttat ctggtcgtgc tccaacgggt        120

<210> SEQ ID NO 11
<211> LENGTH: 120
<212> TYPE: DNA
<213> ORGANISM: Human papillomavirus

<400> SEQUENCE: 11
gtcttcattg tttatggttt accgcactcc aaaaacggtt tgcccaaaaa cggtttgcca        60
accgcagtta gaacttgttt caatttactg ccaaacttat ctggtcgtgc tccaacgggt        120

<210> SEQ ID NO 12
<211> LENGTH: 120
<212> TYPE: DNA
<213> ORGANISM: Human papillomavirus

<400> SEQUENCE: 12
gtcttcattg tttatggttt accacactcc aaaaacaatt tgcccaaaaa cagtttacca        60
accacagtta agacttgttt caatttgctg ccaaacttat ctggtcgtgc tccaacgggt        120

<210> SEQ ID NO 13
<211> LENGTH: 120
<212> TYPE: DNA
<213> ORGANISM: Human papillomavirus

<400> SEQUENCE: 13
gtcttcattg tttatggttt accgcgctcc aaaaacagtt tgcccaaaaa cggtttgcca        60
accgcagtta aaacttgttt caatttgctg ccaaacttat ctggtcatgc tccaacaagt        120

<210> SEQ ID NO 14

```
<211> LENGTH: 120
<212> TYPE: DNA
<213> ORGANISM: Human papillomavirus

<400> SEQUENCE: 14
atcttcatta tttataattt accacactcc aaaaacaatt tacccaaaaa caatttacca      60
accacaatta aaacttattt caatttacta ccaaactttat ctaatcatac tctaacaagt    120

<210> SEQ ID NO 15
<211> LENGTH: 120
<212> TYPE: DNA
<213> ORGANISM: Human papillomavirus

<400> SEQUENCE: 15
gtttttattg tttatggttt accgcgctcc aaagacggtt tgtccaaaga cggtttgcca      60
accgcggtta ggacttgttt taatttgctg ccaaacttgt ctggtcgtgc tccaacgggt    120

<210> SEQ ID NO 16
<211> LENGTH: 120
<212> TYPE: DNA
<213> ORGANISM: Human papillomavirus

<400> SEQUENCE: 16
gtttttattg tttatggttt accgcgctct aaagatggtt tgcttaaaga cggtttgcta      60
accgcggtta ggacttgttt caatttgctg ccaaacttat ctggtcgtgc tccaacgggt    120

<210> SEQ ID NO 17
<211> LENGTH: 120
<212> TYPE: DNA
<213> ORGANISM: Human papillomavirus

<400> SEQUENCE: 17
gtttttattg tttatggttt accgcgcttt aaagacggtt tgcctaaaga cggtttgcta      60
accgcggtta ggacttgttt caatttgctg ccaaacttat ctggtcgtgc tccaacgggt    120

<210> SEQ ID NO 18
<211> LENGTH: 120
<212> TYPE: DNA
<213> ORGANISM: Human papillomavirus

<400> SEQUENCE: 18
gtttttattg tttatggttt actgcgcttt aaagacggtt tgcctaaaga cggtttgcta      60
actgcggtta ggacttgttt taatttgctg ccaaacttat ttggtcgtgc tccaacgggt    120

<210> SEQ ID NO 19
<211> LENGTH: 120
<212> TYPE: DNA
<213> ORGANISM: Human papillomavirus

<400> SEQUENCE: 19
gtttttattg tttatggttt accgcgcttt aaagacggtt tgcctaaaga cggtttgcta      60
accgcggtta ggacttgttt taatttgctg ccaaacttat ttggttgtgc tttaacgggt    120

<210> SEQ ID NO 20
<211> LENGTH: 225
<212> TYPE: DNA
<213> ORGANISM: Human papillomavirus

<400> SEQUENCE: 20
caactaaatg tcaccctagt tcatacatga actgtgtaaa ggttagtcat acattgttca      60
```

```
tttgtaaaac tgcacatggg tgtgtgcaaa ccgttttggg ttacacattt acaagcaact      120
tatataataa tactaaacta caataattca tgtataaaac taagggcgta accgaaatcg      180
gttgaaccga aaccggttag tataaaagca gacattttat gcacc                     225

<210> SEQ ID NO 21
<211> LENGTH: 225
<212> TYPE: DNA
<213> ORGANISM: Human papillomavirus

<400> SEQUENCE: 21
caactaaatg tcaccctagt tcatacatga actgtgtaaa ggttagtcat acattgttca       60
tttgtaaaac tgcacatgag tgtgtgcaaa ccgttttagg ttacacattt acaagcaact      120
tatataataa tactaaacta caataattca tgtataaaac taagagcgta accaaaatca      180
gttgaaccga aaccggttag tataaaagca aacattttat gcacc                     225

<210> SEQ ID NO 22
<211> LENGTH: 225
<212> TYPE: DNA
<213> ORGANISM: Human papillomavirus

<400> SEQUENCE: 22
caactaaatg tcaccctagt tcatacataa actgtgtaaa ggttagtcat acattgttca       60
tttgtaaaac tgcacatggg tgtgtgcaaa ccgttttggg ttacacattt acaagcaact      120
tatataataa tactaaacta caataattca tgtataaaac taagggcgta accgaaatcg      180
gttaaaccaa aaccggttag tataaaagca aacattttat gcacc                     225

<210> SEQ ID NO 23
<211> LENGTH: 225
<212> TYPE: DNA
<213> ORGANISM: Human papillomavirus

<400> SEQUENCE: 23
caactaaatg tcaccctagt tcatacataa actgtgtaaa ggttagtcat acactgttca       60
tttgtaaaac tgcacatagg tgtgtacaaa ccgttttaag ttacacattt acaagcaact      120
tatataataa tactaaacta caataattca tgtataaaac taagggcgta accaaaatcg      180
gttaaaccaa aaccggttag tataaaagca gacattttat gcacc                     225

<210> SEQ ID NO 24
<211> LENGTH: 225
<212> TYPE: DNA
<213> ORGANISM: Human papillomavirus

<400> SEQUENCE: 24
caactaaatg tcaccctagt tcatacatga actgtgtaaa gattagtcat acattgttca       60
tttgtaaaac tgcacataag tgtgtgcaaa ccgttttggg ttacacattt acaagcaact      120
tatataataa tactaaacta caataattca tgtataaaac taaaagcgta accaaaatca      180
gttaaaccaa aaccagttag tataaaagca gacattttat gcacc                     225

<210> SEQ ID NO 25
<211> LENGTH: 225
<212> TYPE: DNA
<213> ORGANISM: Human papillomavirus

<400> SEQUENCE: 25
caactaaatg tcaccctagt tcatacataa actatgtaaa ggttagtcat acattgttca       60
```

| | | |
|---|---|---|
| tttgtaaaac tgcacataag tgtgtgcaaa ccgttttggg ttacacattt acaagcaact | 120 | |
| tatataataa tactaaacta caataattca tgtataaaac taaaagcgta accaaaatca | 180 | |
| gttaaaccaa aaccagttag tataaaagca gacattttat gcacc | 225 | |

<210> SEQ ID NO 26
<211> LENGTH: 225
<212> TYPE: DNA
<213> ORGANISM: Human papillomavirus

<400> SEQUENCE: 26

| | |
|---|---|
| taactaaatg tcaccctagt tcatacatga actgtgtaaa ggttagtcat acattgttca | 60 |
| tttgtaaaac tgcacatggg tgtgtgcaaa ccgttttggg ttacacattt acaagtaact | 120 |
| tatataataa tactaaacta caataattca tgtataaaac taagggcgta accgaaatcg | 180 |
| gttgaaccga aaccggttag tataaaagca gatattttat gcacc | 225 |

<210> SEQ ID NO 27
<211> LENGTH: 225
<212> TYPE: DNA
<213> ORGANISM: Human papillomavirus

<400> SEQUENCE: 27

| | |
|---|---|
| taactaaatg ttatcctagt tcatacatga gctgtgtaaa ggttagtcat acattgttca | 60 |
| tttgtaaaac tgcacatggg tgtgtgcaaa ccgttttggg ttacacattt acaagcaact | 120 |
| tatataataa tactaaacta caataattca tgtataaaac taagggcgta accgaaatcg | 180 |
| gttgaaccga aaccggttag tataaaagca gacattttat gcacc | 225 |

<210> SEQ ID NO 28
<211> LENGTH: 225
<212> TYPE: DNA
<213> ORGANISM: Human papillomavirus

<400> SEQUENCE: 28

| | |
|---|---|
| taactaaatg tcatcctagt tcatacatga actatgtaaa ggttagtcat acattgttca | 60 |
| tttgtaaaac tgcacatggg tgtgtgcaaa ccgttttggg ttacacattt acaagcaact | 120 |
| tatataataa tactaaacta caataattca tgtataaaac taagggcgta accgaaattg | 180 |
| gttgaaccga aaccggttag tataaaagca gacattttat gcacc | 225 |

<210> SEQ ID NO 29
<211> LENGTH: 325
<212> TYPE: DNA
<213> ORGANISM: Human papillomavirus

<400> SEQUENCE: 29

| | |
|---|---|
| ctatgcgcca acgccttaca taccgctgtt aggcacatat ttttggcttg ttttaactaa | 60 |
| cctaattgca tatttggcat aaggtttaaa cttctaaggc caactaaatg tcaccctagt | 120 |
| tcatacatga actgtgtaaa ggttagtcat acattgttca tttgtaaaac tgcacatggg | 180 |
| tgtgtgcaaa ccgttttggg ttacacattt acaagcaact tatataataa tactaaacta | 240 |
| caataattca tgtataaaac taagggcgta accgaaatcg gttgaaccga aaccggttag | 300 |
| tataaaagca gacattttat gcacc | 325 |

<210> SEQ ID NO 30
<211> LENGTH: 325
<212> TYPE: DNA
<213> ORGANISM: Human papillomavirus -continued

```
<400> SEQUENCE: 30
ctatgcgcca acgccttata taccgctgtt aggcacatat ttttggcttg ttttaactaa       60
cctaattgta tatttggcat aaggtttaaa cttttaaggc caactaaatg tcaccctagt      120
tcatacatga actgtgtaaa ggttagtcat acattgttta tttgtaaaac tgcacatggg      180
tgtgtgcaaa ccgttttggg ttacacattt ataagcaatt tatataataa tactaaacta      240
caataattta tgtataaaac taagggcgta accgaaatcg gttgaatcga aaccggttag      300
tataaaagta gacattttat gcacc                                            325
```

APOBEC3 MEDIATED DNA EDITING

1. INTRODUCTION

The present invention relates to methods and compositions for preventing the occurrence or progression of a cancer or pre-cancerous condition associated with expression, or over-expression of human cytidine deaminases of the APOBEC3 family. Such cytidine deaminases, include for example, APOBEC3A (herein after referred to as hA3A), APOBEC3C (herein after referred to as hA3C) and APOBEC3H (herein after referred to as hA3H). The invention also relates to drug screening assays designed to identify compounds that regulate the activity, or level of expression, of hA3A, hA3C and hA3H. In a specific embodiment of the invention, such screening assays may be used to identify potential compounds capable of inhibiting genomic mutagenesis. In yet another embodiment of the invention, such screening, assays may be used to identify potential carcinogenic or mutagenic compounds. The invention further relates to transgenic mice, as well as cells derived from said mice, that have been genetically engineered to express, or over-express hA3A, hA3C and/or hA3H. Such mice may be utilized to screen for, or identify, compounds that modulate the activity, or expression, of the human cytidine deaminases. The present invention also provides topical compositons such as cosmetic lotion, crème, or sunscreen for use on the skin, which comprise one or more inhibitors of human cytidine deaminase activity. The invention is based on the discovery that expression of the hA3A, hA3C and hA3H genes in HPV infected cells is associated with hyperedited HPV DNA.

2. BACKGROUND OF INVENTION

In humans, there is a locus on chromosome 22 that encodes 7 APOEBC3 genes encoding APOBEC3A (A3), A3B, A3C, A3DE, A3F, A3G and A3H. To distinguish them from those in other animals they are generally abbreviated to hA3A, hA3B, hA3C, hA3DE, hA3F, hA3G and hA3H. While there is still much work to do defining substrate specificity for the ensemble of these enzymes, it is clear that all seven are capable of deaminating cytidine residues in single stranded DNA.

Some of these APOBEC3 deaminases have been demonstrated to have anti-retroviral effects (Lecossier et al., 2003, Mangeat et al., 2003, Mariani et al., 2003, Suspene et al., 2004, Zhang et al., 2003). Human immunodeficiency virus type (HIV-1) cDNA in particularly is vulnerable to the action of the cytoplasmic hA3F and hA3G cytidine deaminases (hA3F & hA3G) (Harris et al., 2003, Wiegang et al., 2004). By contrast hA3A, hA3C and hA3H are mainly nuclear while hA3B is both nuclear and cytoplasmic (Bogerd et al., 2006, Kinomoto et al., 2007).

Human A3A and hA3B are expressed in psoriatic keratinocytes and hA3A is up-regulated in acne lesions and can be induced by phorbol-12-myristate 13-acetate (Madsen et al., 1999, Trivedi et al., 2006). Interestingly, hA3H is also expressed in normal skin (Dang et al., 2006, OhAinle et al., 2006).

3. SUMMARY OF THE INVENTION

The present invention relates to methods and compositions for modulating the expression or activity of APOBEC 3A, APOBEC 3C or APOBEC 3H. Such methods and compositions may be used for preventing the occurrence or progression of a cancer or pre-cancerous condition associated with expression, or over-expression of human cytidine deaminases of the APOBEC3 family. Such cytidine deaminases, include for example, APOBEC3A (herein after referred to as hA3A), APOBEC3C (herein after referred to as hA3C) and APOBEC3H (herein after referred to a hA3H). The method comprises administering to a mammal a compound that inhibits the activity of hA3A, hA3C and hA3H in an amount effective to prevent the occurrence of cancer (carcinogenesis) or a precancerous condition, or to slow or halt the progression of cancer or precancerous conditions. The chemopreventive compositon can be administered as a therapeutic to treat an existing condition or as a prophylactic in advance of exposure to a carcinogenic compound or event.

The invention also relates to drug screening assays designed to identify compounds that regulate the activity, or level of expression, of hA3A, hA3C and hA3H. In a specific embodiment of the invention, such screening assays may be used to identify potential compounds capable of inhibiting mutagenesis. In yet another embodiment of the invention, such screening assays may be used to identify potential carcinogenic or mutagenic compounds.

The invention further relates to transgenic mice, as well as cells derived from said mice, that have been genetically engineered to express, or over-express hA3A, hA3C and/or hA3H. Such mice may be utilized to screen for, or identify, compounds that modulate the activity, or expression, of the human cytidine deaminases.

The present invention also provides topical compositions such as cosmetic lotion, crème, or sunscreen for use on the skin, which comprise one or more inhibitors of human cytidine deaminase activity.

4. BRIEF DESCRIPTION OF THE FIGURES

FIG. 1. APOBEC3 editing of HPVIa genomes in vivo and in vitro A) A selection of G→A and C→T edited HPV1a sequences derived from a plantar wart (sample HPV1-a −1). Only sequences differences are noted with respect to the viral plus strand (SEQ ID NOs: 9-19). For clarity, only the most 5' 120 bases of the 315 by segment are shown. The number to the right indicates the total number of edited bases per sequence. B) Mutation matrices for the edited HPV1-a genomes in vivo and in vitro. The number of bases sequenced is shown below each matrix. C) 3' Dinucleotide context analysis of in vivo edited HPV sequences. The cytidine target is underlined. The expected values were calculated for both strands and weighted by the number of G→A and C→T edited genomes. D) 5' Dinucleotide context analysis of G→A hypermutated HPV genomes in vivo and in vitro.

Figure 2:
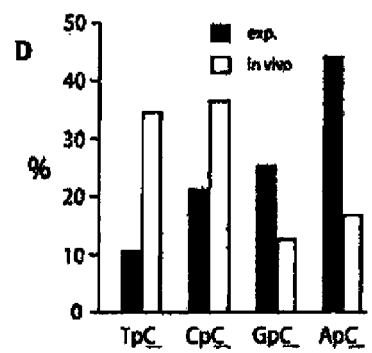
Figure 2:
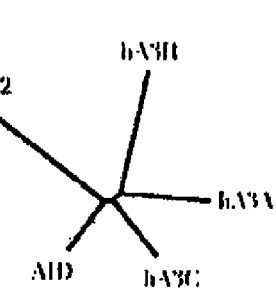

FIG. 2. APOBEC3 editing of HPV16 genomes in vivo A) A selection of G→A and C→T edited HPV 16 sequences derived from pre-cancerous cervical biopsies from sample HPV 16-29. Only sequences differences are noted with respect to the viral plus strand (SEQ ID NOs: 20-28). For clarity, only the most 5' 225 bases of the 325 bp by segment are shown. The number to the right indicates the total number of edited bases per sequence. B) C→T hypermutated sequence derived from pre-cancerous cervical biopsy HPV16-33, the complete region being shown (SEQ ID NOs: 29-30). The unedited reference sequence for samples 29 and 33 is identical to that of AF067024. C) Mutation matrices for the edited HPV-16 genomes in vivo. The number of bases sequenced is shown below each matrix. D) 5' Dinucleotide context analysis of hyperedited HPV16 genomes in vivo E)

Neighbor-Joining tree of five human single domain cytidine deaminases including hAPOBEC2, hA2).

5. DETAILED DESCRIPTION OF THE INVENTION

The present invention relates to methods and compositions for preventing the occurrence or progression of a cancer or pre-cancerous condition associated with expression, or over-expression of human cytidine deaminases of the APOBEC3 family. The invention also relates to drug screening assays designed to identify compounds that regulate the activity, or level of expression, of hA3A, hA3C and hA3H. The invention further relates to transgenic mice, as well as cells derived from said mice, that have been genetically engineered to express, or over-express hA3A, hA3C and/or hA3H. Such mice may be utilized to screen for, or identify, compounds that modulate the activity, or expression, of the human cytidine deaminases. The present invention also provides topical compositions such as cosmetic lotion, crème, or sunscreen for use on the skin, which comprise one or more inhibitors of human cytidine deaminase activity.

5.1 Edited Nucleic Acid Molecules

As described herein, the present invention relates to the discovery that human cytidine deaminases of the APOBEC3 family, i.e., hA3A, hA3C or hA3H, are associated with the presence of hyper-edited DNA. Accordingly, the present invention relates to a double stranded cellular or non-cellular DNA molecules following opening up of its duplex structure, said DNA being edited with a cellular protein normally or abnormally expressed in the nucleus of an eukaryotic cell. The present invention encompasses an edited DNA molecule which is an origin of replication of a gene or a gene or a part of a gene or an exon or a siRNA gene.

The invention is also relates to a single stranded DNA obtained or derived from the double stranded DNA after the opening up of its duplex structure and editing by a cellular protein normally or abnormally expressed in the nucleus of an eukaryotic cell. Specifically, the invention relates to a double stranded viral DNA edited following opening up of its duplex structure with a cellular protein normally or abnormally expressed in the nucleus of an eukaryotic cell. The double or the single stranded DNA according to the invention, is mutated or hypermutated compared to their normal sequences of reference.

In a specific embodiment of the invention, the double stranded or the single stranded DNA obtained according to the invention is derived or mutated from normal viral nucleic acids sequences corresponding to the viral genomes or the cDNA from at least one of the following viruses: cytomegalovirus, herpes simplex 1 and 2, Epstein-Barr virus, human herpes virus 1, 2, 3, 4, 5, 6, 7 and 8, adenoviruses, human and animal papillomaviruses, BK virus and JC virus.

As an example, an edited double stranded or single stranded DNA is related to a part of the genome of a human papillomavirus.

The present invention relates to methods of preparation, isolation and detection of such double or single edited DNAs according to the invention. The present invention further relates to a double stranded DNA molecule obtained following opening up of its duplex structure, said DNA being edited with a cellular protein normally or abnormally expressed in the nucleus of an eukaryotic cell. The mono-stranded DNA derived from the said double stranded DNA is also encompassed by the present invention.

5.2. Screening Assays for Compounds Useful in Modulating the Activity of hA3A, hA3C and hA3H The present invention relates to screening assay systems designed to identify compounds or compositions that modulate the DNA editing activity of human cytidine deaminases of the APOBEC3 family, in particular, APOBEC3A, APOBEC3C and APOBEC3H. Such compounds may be useful for preventing the occurrence or progression of a cancer or precancerous condition.

5.2.1. Recombinant Expression of Cytidine Deaminases

For purposes of developing screening assays designed to identify compounds or compositions that modulate hA3A, hA3C and/or hA3H enzymatic activity or the replication or transcription of the corresponding genes or cDNA it may be necessary to recombinantly express said cytidine deaminase proteins. The cDNA sequence and deduced amino acid sequence of APOBEC3A is disclosed in Jarmuz et al. (Genomics, 2002, Vol. 79, p. 285-296. The cDNA sequence and deduced amino acid sequence of APOBEC3C is disclosed in Jarmuz et al. (Genomics, 2002, Vol. 79, p. 285-296. The cDNA sequence and deduced amino acid sequence of APOBEC3H is described by OhAinle et al. in J. Virol. 2006, Vol. 80, p. 3853.

Nucleotide sequences may be isolated using a variety of different methods known to those skilled in the art. For example, a cDNA library constructed using RNA from a tissue known to express the specific cytidine deaminases can be screened using a labeled probe. Alternatively, a genomic library may be screened to derive nucleic acid molecules encoding the cytidine deaminase protein of interest. Further, cytidine deaminase nucleic acid sequences may be derived by performing a polymerase chain reaction (PCR) using two oligonucleotide primers designed on the basis of known cytidine deaminase nucleotide sequences. The template for the reaction may be cDNA obtained by reverse transcription of mRNA prepared from cell lines or tissue known to express the cytidine deaminase.

Proteins, polypeptides and peptide fragments, mutated, truncated or deleted forms of the hA3A, hA3C and hA3H cytidine deaminases and/or cytidine deaminase fusion proteins can be prepared for a variety of uses, including but not limited to the generation of antibodies, the identification of other cellular gene products involved in the regulation of cytidine deaminase mediated DNA editing, and the screening for compounds that can be used to modulate DNA editing. Cytidine deaminase fusion proteins include fusions to an enzyme, fluorescent protein, a polypeptide tag or luminescent protein which provide a marker function.

While the hA3A, hA3C and hA3H cytidine deaminase polypeptides and peptides can be chemically synthesized (e.g., see Creighton, 1983, Proteins: Structures and Molecular Principles, W.H. Freeman & Co., N.Y.), large polypeptides and the full length cytidine deaminases themselves may be advantageously produced by recombinant DNA technology using techniques well known in the art for expressing a nucleic acid containing cytidine deaminase gene sequences and/or coding sequences. Such methods can be used to construct expression vectors containing hA3A, hA3C and hA3H cytidine deaminase nucleotide sequences and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the hA3A, hA3C and hA3H cytidine deaminase nucleotide sequences. Where the cytidine deaminase peptide or polypeptide is expressed as a soluble protein or derivative (e.g., peptides corresponding to the intracellular or extracellular domain) and is not secreted, the peptide or polypeptide can be recovered from the host cell. Alternatively, where the cytidine deaminase peptide or polypeptide is secreted the peptide or polypeptides may be recovered from the culture media. Such engineered host cells themselves may be used in situations where it is important not only to retain the structural and functional characteristics of the cytidine deaminases, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing hA3A, hA3C and hA3H cytidine deaminase nucleotide sequences; yeast transformed with recombinant yeast expression vectors containing said cytidine deaminase nucleotide sequences or mammalian systems harboring recombinant expression constructs containing promoters derived from the genome of mammalian cells or from mammalian or insect viruses.

Appropriate expression systems can be chosen to ensure that the correct modification, processing and sub-cellular localization of the hA3A, hA3C and hA3H cytidine deaminase proteins occurs. To this end, eukaryotic host cells which possess the ability to properly modify and process the cytidine deaminase proteins are preferred. For long-term, high yield production of recombinant cytidine deaminase proteins, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered cells may be allowed to grow for 1-2 days in enriched media, and then switched to a selective media. Such engineered cell lines may be particularly useful in screening and evaluation of compounds that modulate the endogenous activity of the hA3A, hA3C and hA3H cytidine deaminase gene products.

5.2.2. Non-Cell Based Assays

In accordance with the invention, non-cell based assay systems may be used to identify compounds that interact with, i.e., bind to hA3A, hA3C and hA3H cytidine deaminases, and regulate the enzymatic activity of said cytidine deaminases. Such compounds may act as antagonists or agonists of cytidine deaminase enzyme activity and may be used to regulate the level of DNA editing, i.e., mutagenesis. Recombinant hA3A, hA3C and hA3H cytidine deaminases, including peptides corresponding to different functional domains, or cytidine deaminase fusion proteins, may be expressed and used in assays to identify compounds that interact with cytidine deaminases.

To this end, soluble hA3A, hA3C and hA3H cytidine deaminases maybe recombinantly expressed and utilized in non-cell based assays to identify compounds that bind to said cytidine deaminases. Recombinantly expressed cytidine deaminase polypeptides or fusion proteins may be prepared as described above, and used in the non-cell based screening assays. For example, a full length hA3A, hA3C and hA3H cytidine deaminase, or a soluble truncated cytidine deaminase, or a fusion protein containing a cytidine deaminase polypeptide fused to a protein or polypeptide that affords advantages in the assay system (e.g., labeling, isolation of the resulting complex, etc.) can be utilized.

The principle of the assays used to identify compounds that bind to hA3A, hA3C and hA3H cytidine deaminases involves preparing a reaction mixture of the cytidine deaminase to be assayed and the test compound under conditions and for time sufficient to allow the two components to interact and bind, thus forming a complex which can be removed and/or detected in the reaction mixture. The identity of the bound test compound is then determined. In a further embodiment of the invention, the assay may further comprise testing the ability of the test compound to regulate the DNA editing capability of the compound.

The screening assays are accomplished by any of a variety of commonly known methods. For example, one method to conduct such an assay involves anchoring the cytidine deaminase protein, polypeptide, peptide, fusion protein or the test substance onto a solid phase and detecting cytidine deaminase/test compound complexes anchored on the solid phase at the end of the reaction. In one embodiment of such a method, the cytidine deaminase reactant is anchored onto a solid surface, and the test compound, which is not anchored, may be labeled, either directly or indirectly.

In practice, high throughput screens may be conducted using arrays of reactions. Microtitre plates conveniently can be utilized as the solid phase. The anchored component is immobilized by non-covalent or covalent attachments. The surfaces may be prepared in advance and stored. In order to conduct the assay, the non-immobilized component is added to the coated surfaces containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the solid surface; e.g., using a labeled antibody specific for the previously non-immobilized component.

Alternatively, a reaction is conducted in a liquid phase, the reaction products separated from unreacted components using an immobilized antibody specific for cytidine deaminase protein, fusion protein or the test compound, and complexes detected using a labeled antibody specific for the other component of the possible complex to detect anchored complexes.

In accordance with the invention, non-cell based assays may also be used to screen for compounds that directly inhibit or activate enzymatic activities associated with cytidine deaminases. Such activities include but are not limited to DNA editing activity. To this end, a reaction mixture of the cytidine deaminase and a test compound is prepared in the presence of substrate and the enzymatic activity of cytidine deaminase is compared to the activity observed in the absence of test compound In non-limiting embodiments of the invention, a reaction mixture of the cytidine deaminase, a test compound and substrate is prepared and the activity of the cytidine deaminase is compared to the activity observed in the absence of the test compound wherein decrease in the level of cytidine deaminase enzyme activity in the presence of the test compound indicates that a cytidine deaminase antagonist has been identified. Such compounds may be used for preventing the occurrence or progression of a cancer or precancerous condition.

Alternatively, a reaction mixture of the cytidine deaminase, a test compound and substrate is prepared and the activity of cytidine deaminase is compared to the activity observed in the absence of the test compound wherein an increase in the level of cytidine deaminase enzyme activity in the presence of the test compound indicates that a cytidine deaminase agonist has been identified. Screening for such agonists is designed to identify potential carcinogenic or mutagenic compounds.

5.2.3. Cell Based Assays

In accordance with the invention, a cell based assay system can be used to screen for compounds that modulate the activity of hA3A, hA3C and hA3H cytidine deaminases. In accordance with the invention, a cell-based assay system can be used to screen for compounds that modulate the activity of said cytidine deaminases and thereby, modulate the DNA editing mediated by cytidine deaminase. To this end, cells that endogenously express hA3A, hA3C and hA3H cytidine deaminase can be used to screen for compounds. Such cells include, for example, keratinocytes. Alternatively, cell lines, such as 293 cells, COS cells, CHO cells, fibroblasts, and the like, genetically engineered to express cytidine deaminases can be used for screening purposes.

The present invention provides methods for identifying compounds that alter one of more of the enzymatic activities of hA3A, hA3C and hA3H cytidine deaminase, including but not limited to, DNA editing activity. Specifically, compounds may be identified that promote cytidine deaminase enzyme activities, i.e., agonists, or compounds that inhibit cytidine deaminase enzyme activities, i.e., antagonists. Compounds that inhibit cytidine deaminase enzyme activities will be inhibitory for DNA editing activity and may be used for preventing the occurrence or progression of a cancer or precancerous condition. Compounds that activate cytidine deaminase enzyme activity will be identified as possible mutagenic or carcinogenic compounds.

The present invention provides for methods for identifying a compound that activates cytidine deaminase enzyme activity, comprising (i) contacting a cell expressing cytidine deaminase with a test compound in the presence of substrate and measuring the level of cytidine deaminase activity; (ii) in a separate experiment, contacting a cell expressing cytidine deaminase with a vehicle control and measuring the level of cytidine deaminase activity where the conditions are essentially the same as in part (i), and then (iii) comparing the level of cytidine deaminase activity measured in part (i) with the level of cytidine deaminase activity in part (ii), wherein an increased level of cytidine deaminase activity in the presence of the test compound indicates that the test compound is a cytidine deaminase activator.

The present invention also provides for methods for identifying a compound that inhibits cytidine deaminase enzyme activity comprising (i) contacting a cell expressing cytidine deaminase with a test compound and substrate and measuring the level of cytidine deaminase activity; (ii) in a separate experiment, contacting a cell expressing cytidine deaminase and substrate and measuring the level of cytidine deaminase activity, where the conditions are essentially the same as in part (i) and then (iii) comparing the level of cytidine deaminase measured in part (i) with the level of cytidine deaminase activity in part (ii), wherein a decrease level of cytidine deaminase activity in the presence of the test compound indicates that the test compound is a cytidine deaminase inhibitor.

In utilizing the cell systems described above, such cell systems, the cells expressing the cytidine deaminase protein are exposed to a test compound or to vehicle controls e.g., placebos): After exposure, the cells can be assayed to measure the activity of cytidine deaminase.

The ability of a test molecule to modulate the activity of hA3A, hA3C and hA3H maybe measured using standard biochemical and physiological techniques. In a specific embodiment of the invention, cytidine deaminase activity can be measured using the method disclosed in PCT application WO 2007/091125A2, which is incorporated by reference in its entirety herein.

In a specific embodiment of the invention, a method is provided for identifying a compound that modulates, i.e., inhibits or activates, cytidine deaminase activity comprising (i) contacting a cell expressing cytidine deaminase with a test compound and measuring the level of DNA editing activity; (ii) in a separate experiment, contacting a cell expressing cytidine deaminase protein with a vehicle control in the presence of substrate and measuring the level of cytidine deaminase DNA editing activity where the conditions are essentially the same as in part (i), and then (iii) comparing the level of cytidine deaminase DNA editing activity measured in part (i) with the level of cytidine deaminase DNA editing activity in part (ii), wherein a difference in the level of cytidine deaminase DNA editing activity in the presence of the test compound indicates that the test compound is a cytidine deaminase modulator.

5.2.4. Assay for Compounds that Regulate the Expression of hA3A, hA3C and hA3H In accordance with the invention, a cell based assay system can be used to screen for compounds that modulate the expression of hA3A, hA3C and hA3H cytidine deaminases within a cell. Assays may be designed to screen for compounds that regulate hA3A, hA3C and hA3H cytidine deaminase expression at either the transcriptional or translational level. In one embodiment, DNA encoding a reporter molecule can be linked to a regulatory element of the cytidine deaminase gene and used in appropriate intact cells, cell extracts or lysates to identify compounds that modulate cytidine deaminase gene expression. Such reporter genes may include but are not limited to chloramphenicol acetyltransferase (CAT), luciferase, gamma-glucuronidase (GUS), growth hormone, or placental alkaline phosphatase (SEAP). Such constructs are introduced into cells thereby providing a recombinant cell useful for screening assays designed to identify modulators of hA3A, hA3C and hA3H cytidine deaminase gene expression.

Following exposure of the cells to the test compound; the level of reporter gene expression may be quantitated to determine the test compound's ability to regulate cytidine deaminase expression. Alkaline phosphatase-assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemiluminescent assays such as those described in Bronstein, I. et al. (1994, *Biotechniques* 17: 172-177). Such assays provide a simple, sensitive easily automatable detection system for pharmaceutical screening.

To identify compounds that regulate hA3A, hA3C and hA3H cytidine deaminase translation, cells or in vitro cell lysates containing cytidine deaminase transcripts maybe tested for modulation of mRNA translation. To assay for inhibitors of cytidine deaminase translation, test compounds are assayed for their ability to modulate the translation of cytidine deaminase mRNA in in vitro translation extracts.

In an embodiment of the invention, the level of hA3A, hA3C and hA3H cytidine deaminase expression can be modulated using antisense, ribozyme, or RNAi approaches to inhibit or prevent translation of hA3A, hA3C and hA3H cytidine deaminase mRNA transcripts or triple helix approaches to inhibit transcription of the cytidine deaminase gene. Such approaches may be utilized to treat disorders such as proliferative disorders where inhibition of cytidine deaminase expression is designed to prevent DNA editing which can be associated with hypermutation of the genome leading to cancer.

Antisense and RNAi approaches involve the design of oligonucleotides (either DNA or RNA) that are complementary to hA3A, hA3C and hA3H cytidine deaminase mRNA. The antisense or RNAi oligonucleotides will be targeted to the complementary mRNA transcripts and prevent translation. Absolute complementarity, although preferred, is not required. One skilled in the art can ascertain a tolerable degree of mismatch by use of standard procedures to determine the melting point of the hybridized complex.

In yet another embodiment of the invention, ribozyme molecules designed to catalytically cleave hA3A, hA3C and hA3H cytidine deaminase mRNA transcripts can also be used to prevent translation of said cytidine deaminase mRNA and expression of cytidine deaminases. (See, e.g., PCT International Publication WO90/11364, published Oct. 4, 1990; Sarver et al., 1990, Science 247:1222-1225). Alternatively, endogenous cytidine deaminase gene expression can be reduced by targeting deoxyribonucleotide sequences complementary to the regulatory region of the cytidine deaminase genes (i.e., the cytidine deaminase promoter and or enhancers) to form triple helical structures that prevent transcription of the cytidine deaminase gene in targeted hematopoietically-derived cells in the body. (See generally, Helene, C. et al., 1991, Anticancer Drug Des. 6:569-584 and Maher, L J, 1992, Bioassays 14:807-815).

In a preferred embodiment of the invention, double-stranded short interfering nucleic acid (siNA) molecules may be designed to inhibit hA3A, hA3C and/or hA3H cytidine deaminase expression. In one embodiment, the invention features a double-stranded siNA molecule that down-regulates expression of the hA3A, hA3C and/or hA3H cytidine deaminase gene product, wherein said siNA molecule comprises about 15 to about 28 base pairs.

In one embodiment, the invention features a double stranded short interfering nucleic acid (siNA) molecule that directs cleavage of a hA3A, hA3C and hA3H cytidine deaminase RNA via RNA interference (RNAi), wherein the double stranded siNA molecule comprises a first and a second strand, each strand of the siNA molecule is about 18 to about 28 nucleotides in length, the first strand of the siNA molecule comprises nucleotide sequence having sufficient complementarity to the hA3A, hA3C or hA3H cytidine deaminase RNA for the siNA molecule to direct cleavage of the hA3A, hA3C or hA3H cytidine deaminase RNA via RNA interference, and the second strand of said siNA molecule comprises nucleotide sequence that is complementary to the first strand.

The oligonucleotides of the invention, i.e., antisense, ribozyme and triple helix forming oligonucleotides, may be synthesized by standard methods known in the art, e.g., by use of an automated DNA synthesizer (such as are commercially available from Biosearch, Applied Biosystems, etc.). Alternatively, recombinant expression vectors may be constructed to direct the expression of the oligonucleotides of the invention. Such vectors can be constructed by recombinant DNA technology methods standard in the art. In a specific embodiment, vectors such as viral vectors may be designed for gene therapy applications where the goal is in vivo expression of inhibitory oligonucleotides in targeted cells.

5.2.5. Compounds that can be Screened in Accordance with the Invention

The assays described above can identify compounds which modulate cytidine deaminase activity. For example, compounds that affect cytidine deaminase activity include but are not limited to compounds that bind to cytidine deaminase, and either activate enzyme activities (agonists, mutagenic or carcinogenic compounds) or block enzyme activities (antagonists). Alternatively, compounds may be identified that do not bind directly to cytidine deaminases but are capable of altering cytidine deaminase enzyme activity by altering the activity of a protein that regulates cytidine deaminase enzyme activity.

The compounds which may be screened in accordance with the invention include, but are not limited to, small organic or inorganic compounds, peptides, antibodies and fragments thereof, and other organic compounds e.g., peptidomimetics) that bind to hA3A, hA3C and hA3H cytidine deaminase and either mimic the activity triggered by any of the known or unknown substrates of hA3A, hA3C and hA3H cytidine deaminase (i.e., agonists) or inhibit the activity triggered by any of the known or unknown substrates of hA3A, hA3C and hA3H cytidine deaminase (i.e., antagonists).

Compounds may include, but are not limited to, peptides such as, for example, soluble peptides, including but not limited to members of random peptide libraries (see, e.g., Lam, K. S. et al., 1991, Nature 354:82-84; Houghten, R. et al., 1991, Nature 354:84-86); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., 1993, Cell 72:767-778), antibodies (including, but not limited to, polyclonal, monoclonal, humanized, anti-idiotypic, chimeric or single chain antibodies, and Fab, $F(ab')_2$ and Fab expression library fragments, and epitope binding fragments thereof), and small organic or inorganic molecules.

Other compounds which maybe screened in accordance with the invention include but are not limited to small organic molecules that affect the expression of the hA3A, hA3C and hA3H cytidine deaminase gene or some other gene involved in hA3A, hA3C and hA3H cytidine deaminase activity (e.g., by interacting with the regulatory region or transcription factors involved in gene expression); or such compounds that affect the enzyme activities of hA3A, hA3C and hA3H cytidine deaminase or the activity of some other factor involved in modulating hA3A, hA3C and hA3H cytidine deaminase activity.

5.3. Compositions Containing Modulators of Cytidine Deaminase and their Uses The present invention provides for methods of inhibiting DNA-editing activity, i.e., genomic hypermutation, comprising contacting a cell expressing cytidine deaminase with an effective amount of a cytidine deaminase modulating compound, such as a cytidine deaminase antagonist identified using the assays as set forth supra. An "effective amount" of the cytidine deaminase inhibitor, i.e., antagonist, is an amount that decreases DNA editing enzyme activity as measured by one of the above assays.

The present invention provides for compositions comprising an effective amount of a compound capable of inhibiting the activity of cytidine deaminase, thereby regulating the DNA-editing and genetic hypermutation activity of cells, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The present invention relates to methods and compositions for preventing the occurrence or progression of a cancer or pre-cancerous condition associated with expression, or over-expression of human cytidine deaminases of the APOBEC3 family. Such cytidine deaminases, include for example, APOBEC3A (herein after referred to a hA3A), APOBEC3C herein after referred to a hA3C) and APOBEC3H (herein after referred to a hA3H). The method comprises administering to a mammal a compound that inhibits the activity of hA3A, hA3C and hA3H in an amount effective to prevent the occurrence of cancer (carcinogenesis) or a precancerous condition, or to slow or halt the progression of cancer or precancerous conditions. The chemopreventive compositon can be administered as a therapeutic to treat an existing condition or as a prophylactic in advance of exposure to a carcinogenic compound or event.

The present invention also provides methods and compositions for treating additional conditions including, but are not limited to, aging, acne, psoriasis, allergy and eczemea and rheumatoid arthritis.

The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing hA3A, hA3C and hA3H are exposed to or otherwise administered a therapeutic compound and the effect of such a therapeutic upon cytidine deaminase activity is observed. In a specific embodiment of the invention the ability of a compound to regulate, i.e., activate or inhibit DNA editing may be assayed.

Various delivery systems are known and can be used to administer a compound capable of regulating cytidine deaminase activity, e.g., encapsulation in liposomes, microparticles, microcapsules, recombinant cells capable of expressing the compound, receptor-mediated endocytosis (see, e.g., Wu and Wu, 1987, *J. Biol. Chem.* 262:44294432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers.

The present invention also provides pharmaceutical compositions. Such compositions comprise a therapeutically effective amount of a compound capable of regulating hA3A, hA3C and hA3H cytidine deaminase activity or hA3A, hA3C and hA3H cytidine deaminase expression and a pharmaceutically acceptable carrier. In a specific embodiment, the term "pharmaceutically acceptable" means approved by a regulatory agency of the Federal or a state government or listed in the U.S. Pharmacopeia or other Generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The amount of the compound of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses maybe extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

The invention also provides a pharmaceutical pack or kit comprising one or more containers filled with one or more of the ingredients of the pharmaceutical compositions of the invention, optionally associated with such container(s) can be a notice in the form prescribed by a governmental agency regulating the manufacture, use or sale of pharmaceuticals or biological products, which notice reflects approval by the agency of manufacture, use or sale for human administration.

5.4. Detection Methods hA3A, hA3C and hA3H cytidine deaminase polynucleotides can be used as probes to detect the presence of cytidine deaminase in a sample indicating an increase in DNA editing and a predisposition to genetic hypermutation. Such diagnostic screening methods may be utilized as an indicator of disease progression and/or the efficacy of drug treatment. Nucleic acid (i.e., DNA or RNA) samples for practicing the present invention may be obtained from any suitable source. Typically, the nucleic acid sample will be obtained from a clinical sample of a biological fluid or biological tissue to be assessed as containing the cytidine deaminase sequences. It will be apparent that the present invention also permits the detection of cytidine deaminase nucleic acid sequences in non-clinical samples.

Isolated polynucleotides with nucleic acid sequences encoding cytidine deaminase can be used as probes to detect the presence of target nucleic acid sequences with sequence homology. Oligonucleotide probes or primers of the present invention may be of any suitable length, depending on the particular assay format employed. In general, the oligonucleotide probes or primers are at least 15 nucleotides in length. For example, oligonucleotide probes or primers used for detecting cytidine deaminase are preferably about 20 nucleotides in length. The oligonucleotide probes or primers may be adapted to be especially suited to a chosen nucleic acid amplification system.

Use of probes in detection methods include Northern blots (RNA detection), Southern blots (DNA detection), and dot or slot blots (DNA, RNA). Other detection methods include kits containing probes on a dipstick setup and the like. Examples of hybridization conditions to be used in the diagnostic assays of the invention can be found in Ausubel, F. M. et al., Current protocols in Molecular Biology, John Wily & Sons, Inc., New York, N.Y. (1989). In a non-limiting embodiment of the invention, a nitrocellulose filter is incubated overnight at 68° C. with labeled probe in a solution containing 50% formamide, high salt, either 5×SSC [20×: 3M NaCl/0.3M trisodium citrate] or 5×SSPE [20×: 3.6M NaCl/0.2M $NaH_2PO_4$/0.02M EDTA, pH 7.7]), 5×Denhardt's solution, 1% SDS, and 100 μg/ml denatured salmon sperm DNA. This is followed by several washes in 0.2×SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid. Stringent conditions will be preferably used.

Hybrid molecules formed using the cytidine deaminase probes of the invention can be detected by using a detectable marker which is added to one of the probes. For example, probes can be radiolabeled and detected by autoradiography. Such labels include, but are not limited to $^3H$, $^{125}I$, $^{35}S$, $^{14}C$, and $^{32}P$. Detectable markers may also include ligands, fluorophores, chemiluminescent agents, electrochemical via sensors, time-resolved fluorescence, enzymes, and antibodies.

Amplification methods may also be employed for detection of hA3A, hA3C and hA3H cytidine deaminase nucleic acids. Examples of suitable amplification techniques include, but are not limited to, polymerase chain reaction, ligase chain reaction, strand displacement amplification, transcription-based amplification (see Kwoh et al., 1989, Proc. Natl. Acad. Sci. USA 86, 1173-1177), self-sustained sequence replication (see Guatelli et al., 1990, Proc. Natl. Acad. Sci. USA 87, 1874-1878), the Qβ replicase system (see Lizardi et al., 1988, BioTechnology 6:1197-1202) and NASBA (Malek et al., 1994, Methods Mol. Biol., 28:253-260). In a preferred embodiment, amplification will be carried out using PCR.

The present invention also provides kits for detecting the presence of hA3A, hA3C and hA3H cytidine deaminase nucleic acids in a sample. Such kits comprise reagents that are capable of specific binding to cytidine deaminase nucleic acids. In instances where binding of the reagent to the cytidine deaminase nucleic acid is not capable of direct detection, the kit may further comprise a second reagent capable of detecting such binding.

In accordance with the invention, detection of hA3A, hA3C and hA3H protein in samples derived from a subject can be used to determine levels of cytidine deaminase expression. The detection of hA3A, hA3C and hA3H cytidine deaminase protein in a sample from a subject can be accomplished by any of a number of methods. Preferred diagnostic methods for the detection of cytidine deaminase protein in the biological sample of a subject can involve, for example, immunoassays wherein cytidine deaminase protein is detected by its interaction with a cytidine deaminase specific antibody. Antibodies useful in the present invention can be used to quantitatively or qualitatively detect the presence of cytidine deaminase or antigenic fragments thereof. In addition, reagents other than antibodies, such as, for example, polypeptides that bind specifically to hA3A, hA3C and hA3H cytidine deaminase protein can be used in assays to detect the level of cytidine deaminase protein expression. Alternatively, detection of cytidine deaminase proteins may be accomplished by detection and measurement of levels of biological properties associated with cytidine deaminase proteins, such as for example, cytidine deaminase enzymatic activities such as DNA editing. Immunoassays useful in the practice of the invention include but are not limited to assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

A clinical sample of a biological fluid or biological tissue to be assessed as containing the hA3A, hA3C and hA3H cytidine deaminase protein, such as blood or liver tissue or other biological tissue, is obtained from a subject suspected of being infected. Aliquots of whole tissues, or cells, are solubilized using any one of a variety of solubilization cocktails known to those skilled in the art. For example, tissue can be solubilized by addition of lysis buffer comprising (per liter) 8 M urea, 20 ml of Nonidet P-40 surfactant, 20 ml of ampholytes (pH 3.5-10), 20 ml of 2-mecaptoethanol, and 0.2 mM of phenylmethylsulfonyl fluoride (PMSF) in distilled deionized water. Immunoassays for detecting expression of cytidine deaminase protein typically comprise contacting the biological sample, such as a blood or tissue sample derived from a subject, with an anti-cytidine deaminase antibody under conditions such that an immunospecific antigen-antibody binding reaction can occur, and detecting or measuring the amount of any immunospecific binding by the antibody. In a specific aspect, such binding of antibody, for example, can be used to detect the presence of hA3A, hA3C and hA3H cytidine deaminase proteins wherein the detection of said cytidine deaminase proteins is an indication of a disease condition.

In an embodiment of the invention, the biological sample, such as a tissue extract is brought in contact with a solid phase support or carrier, such as nitrocellulose, for the purpose of immobilizing any proteins present in the sample. The support is then washed with suitable buffers followed by treatment with detectably labeled cytidine deaminase specific antibody. The solid phase support is then washed with the buffer a second time to remove unbound antibody. The amount of bound antibody on the solid support is then determined according to well known methods. Those skilled in the art will be able to determine optional assay conditions for each determination by employing routine experimentation.

One of the ways in which hA3A, hA3C and hA3H cytidine deaminase antibodies can be detectably labeled is by linking the antibody to an enzyme, such as for use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.; Voller, A., et al., 1978, J. Clin. Pathol. 31:507-520; Butler, J. E., 1981, Meth. Enzymol. 73:482-523). The enzyme which is bound to the antibody will react with an appropriate substrate, preferably a chromogenic substrate, in such a manner as to produce a chemical moiety that can be detected, for example, by spectrophotometric, fluorimetric, or by visual means. Enzymes that can be used to detectable label the antibody include, but are not limited to, horseradish peroxidase and alkaline phosphatase. Detection can also be accomplished by colorimetric methods that employ a chromogenic substrate for the enzyme.

Detection of hA3A, hA3C and hA3H cytidine deaminase antibodies may also be accomplished using a variety of other methods. For example, by radioactively labeling the antibodies or antibody fragments, it is possible to detect cytidine deaminase protein expression through the use of a radioimmunoassay (RIA) (see, for example, Weintraub, B., Principles of Radioimmunoassays, Seventh Training Course on Radioligand Assay Techniques, The Endocrine Society, March 1986). The radioactive isotope can be detected by such means as the use of a gamma counter or a scintillation counter or by autoradiography. The antibody may also be labeled with a fluorescent compound. Among the most commonly used fluorescent labeling compounds are fluorescein isothiocyanate, rhodamine, phycoerythrin and fluorescamine. Likewise, a bioluminescent compound may be used to label the cytidine deaminase antibody. The presence of a bioluminescence protein is determined by detecting the presence of luminescence. Important bioluminescence compounds for purposes of labeling are luciferin, luciferase and aequorin.

5.5. Antibodies

The present invention also provide compositions comprising "Antibody" or "antibodies," as well as fragments thereof, that are capable of binding to an epitope of hA3A, hA3C and hA3H cytidine deaminase. An antibody against said cytidine deaminase that decreases its activity can be used therapeutically, diagnostically or in drug screening assays. The term "epitope" refers to an antigenic determinant on an antigen to which an antibody binds. The terms "antibody" and "antibodies" include polyclonal antibodies, monoclonal antibodies, humanized or chimeric antibodies, single chain Fv antibody fragments, Fab fragments, and F(ab).sub.2 fragments.

Antibody fragments that have specific binding affinity for the polypeptide of interest can be generated by known techniques. Such antibody fragments include, but are not limited to, F(ab').sub.2 fragments that can be produced by pepsin digestion of an antibody molecule, and Fab fragments that can be generated by deducing the disulfide bridges of F(ab').sub.2 fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay (RIA). See, Short Protocols in Molecular Biology eds. Ausubel et al., Green Publishing Associates and John Wiley & Sons (1992). Suitable antibodies typically have equal binding affinities for recombinant and native proteins.

5.6. Transgenic Mice

A transgenic mouse is provided which overexpress one or more human cytidine deaminases, i.e., hA3A, hA3C and hA3H. Such a transgenic mouse genome carries heterogeneous cDNA encoding cytidine deaminase within its genome under the control of a regulatory element capable of inducing expression said deaminase in a mouse cell. Alternatively, in a specific embodiment of the invention, the expression of the one or more cytidine deaminase genes is under the control of its own endogenous promoter. In yet another embodiment, the gene is placed under the control a promoter expressed in keratinocytes. Constructs for use in generating such a mouse include one comprising the cDNA for cytidine deaminase under the control of skin specific promoter, i.e., a keratinocyte specific promoter. Cells, including keratinocytes, may be isolated from such transgenic animals.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

Clones of the non-human transgenic animals described herein can also be produced according to the methods described in Wilmut et al. (1997) Nature 385:81 0-813 and PCT International Publication Nos. WO 97/07668 and WO 97/07669. Transgenic animals containing recombinant cells that express the polypeptides described herein are useful to conduct the assays described herein in an in vivo or in vitro context.

EXAMPLES

The invention is illustrated herein by the experiments described above and by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure of the hA3A, hA3C and hA3H genes will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

6. Example

The following example demonstrates the editing of human papillomavirus DNA by APOBEC3 in benign and precancerous lesions.

6.1 Materials and Methods

Samples. All 6 planta warts have been previously shown to be WPV1 positive by Southern blotting. They were subsequently confirmed as HPV1a. Approximately 0.5 µg of total DNA was used as input material for the amplification of a 482 by fragment of the HPV a genome using standard PCR conditions. The primers were:

```
                                              (SEQ ID NO.: 1)
5HPV1 aout    5'TATTAACACCGCACCCGTTGTRRCTAAT;
and (SEQ ID NO.: 2)
3HPV1 aout    5'CATCAATATATGGGATACAGAGGYTTT.
```

A smaller 370 by fragment was subsequently amplified by 3D-PCR using an 80-90° C. denaturation temperature gradient. The inner primers were:

```
                                              (SEQ ID NO.: 3)
5HPV1 ain     5'TTAAAAGACTACACCTACARRATGTATT;
and (SEQ ID NO.: 4)
3HPV1 ain     5'GTGCAGAGTCTTACCTGTGTATTTTAT.
```

3D-PCR products corresponding to the lowest Td for all six plantar wart samples were cloned and 20-30 clones sequenced per sample.

Approximately 0.5 µg of total DNA was used as input material for the amplification of a 531 bp fragment of the HPV16 genome using primers

```
                                              (SEQ ID NO.: 5)
5'HPV16out    5'TGCTTGCCAACCATTCCATTGTTTTTT;
and (SEQ ID NO.: 6)
3'HPV16out    5'TTGCTTGCAGTACACACATTCTAATATT.
```

A smaller 383 bp fragment was subsequently amplified by 3D-PCR using an 80-83° C. denaturation temperature gradient, using inner primers were;

```
                                              (SEQ ID NO.: 7)
5HPV16in      5'GTACATTGTGTCATATAAAATAAATCA;
and (SEQ ID NO.: 8)
3HPV16in      5'TGTGGGTCCTGAAACATTGCAGTTCTCTTTT.
```

3D-PCR products corresponding to the lowest Td (81.8° C.) for all nine pre-cancerous lesions samples were cloned and sequenced.

Transfections. The HPV1a molecular clone and sequence have been reported (accession number NC001356). The BamHI cloning site is ~3 kb from the origin of replication/viral promoter region and disrupts the 3' part of the E2 and E4 orfs. Hence there is no HPV replication. Approximately $3\times10^6$ 293T cells were co-transfected by 1.5 µg of HPV1a DNA and 2.5 µg of a functional clone of h3A, hA3B, hA3C, hA3F, hA3G, hA3H, hA1, hA2, mA1, mA2 and mA3 using FuGENE 6. After 72 hours the cells were trypsinized and DNA extracted. All transfections were performed twice.

Phylogenic analyses. Amino acid sequences were aligned by CLUSTAL W, Sequence distances were determined with Protdist of the Phylip package version 15, while the Neighbor-Joining method was applied to pairwise distances using the Kimura calculation.

6.2. Results

Total DNA was extracted from 6 HPV1a positive plantar warts. For mutational analysis, a region corresponding to the origin of replication/promoter region was selected, since it seemed likely that this region might exist in a single stranded state more frequently than any other region of the HPV genome. 3D-PCR was used to selectively amplify AT rich edited genomes (Suspene et al., 2005a). This technique described in WO 2007/091125, relies on the fact that AT-rich DNA denatures at a lower temperature than GC-rich DNA, and has proven successful at amplifying APOBEC3 edited retroviral cDNA (Suspène et al., 2005b).

3D-PCR products were cloned and sequenced. For ⅙ plantar warts monotonously G→A or C→T substituted HPV1a sequences were identified (FIGS. 1A, B), demonstrating that both DNA strands had undergone editing. Averaging across both strands, the mean cytidine editing frequency was 11% (range 4-61% per clone). Analysis of the dinucleotide context of edited sites showed that there was no pronounced 3' nucleotide context (FIG. 1C), such as CpG, thus ruling out a cytidine hypermethylation/deamination related phenomenon. By contrast there was a strong 5' effect favouring TpC and CpC typical of some APOBEC3 deaminases (Bishop et al., 2004) (FIG. 1D).

Based on this evidence for in vivo editing of HPV sequences, the potential for APOBEC3 editing of HPV DNA was tested in vitro. Human 293T cells were co-transfected by HPV1a plasmid DNA along with each of six APOBEC3 genes, notably hA3A, hA3B, hA3C, hA3F, hA3G and hA3H cloned in an expression plasmid. At 72 hours, total DNA was recovered and 3D-PCR performed. Compared to the HPV a plasmid plus vector alone transfection (Td=84.6° C.), 3D-PCR products were only recovered at a lower Td (Td=82.0° C.) from the hMA, hA3C and hA3H co-transfections. Sequencing of cloned 3D-PM products showed extensive and monotonous cytidine deamination of both DNA strands (FIG. 1B). The mean cytidine editing frequencies in vitro, 25-29% (range 13-60% per clone), were ~2-fold higher than those in vivo, which may reflect stronger APOBEC3 gene expression driven by the powerful cytomegalovirus immediate early promoter. The ssDNA cytidine editing activity reported here for human hA3H appears to be just as strong as that seen for hA3A and hA3C.

Furthermore, the dinucleotide context of edited sites for all three hA3 deaminases showed a clear 5' preference for TpC and CpC and a strong aversion for ApC that correlates well with the observed editing contexts in vivo (FIG. 1D). As the preferred dinucleotide context for human activation induced cytidine deaminase (AID) is ApC and GpC (Conticello et al., 2005, Pham et al., 2003), it seems probable that this enzyme can be excluded from the list of potential mutators.

Human papillomaviruses can be generally divided into those that infect cutaneous or mucosal keratinocytes, a feature strongly reflected in their phylogenic clustering (De Villiers et als, 2004). Among the latter group are found the HPVs strongly associated with cervical cancer. In a large European study ~65% and ~6% of cervical cancers were associated with HPV16 and HPV18 respectively (Arbyn et al., 2007), with at least 11 other strains also showing a strong association (Congliano et al., 2005).

Although it is not known if APOBEC3 genes are expressed in mucosal keratinocytes, the evidence for APOBEC3 editing of HPV1a genomes suggested examining total DNA from 9 HPV16 positive pre-cancerous cervical biopsies. 3D-PCR was again used to amplify a comparable region spanning the origin of replication/promoter. Cloning and sequencing of the last positive points of sample HPV16-29 yielded 19 sequences with monotonously G→A or C→T transitions indicative of editing of both DNA strands (FIG. 2A). A single C→T edited sequence was also recovered from a second HPV16 sample (HPV16-33, FIG. 2B). A cut-off of >3 C→T transitions was imposed to reduce the impact of natural variation and PCR error in designating APOBEC3 editing. Nonetheless, an analysis of all the remaining HPV16 genomes recovered by 3D-PCR showed a net excess of G→A and C→T transitions (FIGS. 2A, B, C). The mean editing frequency was ~9% (range 5%-24%). Just as for HPV1a in vivo, the preferred dinucleotide context for editing was TpC and CpC suggesting that hA3A/CIH were involved (FIG. 2D).

Transcriptionally active HPV genomes are in the form of mini-chromosomes complete with nucleosomes (Stunkel et al., 1999). If they are as the data suggests, vulnerable to cytidine deamination, say in a subset of cells with over-expressed hA3A/hA3C/hA3H, then it raises the intriguing question as to how chromosomal DNA is normally protected from these three nuclear APOBEC3 deaminases (FIGS. 1, 2). Activation induced deaminase (AID) is a cytidine deaminase that mediates somatic hypermutation of rearranged immuno-globulin genes (Di Noia et al., 2007, Goodman et al., 2007). Not only does this gene have a similar exon/intron structure as hA3A/hA3C/hA3H, but human AID also falls into a cluster with hA3A and hA3C showing ~42-46% amino acid identity (FIG. 2E). By contrast, hA3H shows only 32-34% identity with members of this AID/hA3A/hA3C cluster. Ectopic expression of AID may be found in a variety of cell types including non-lymphoid tumours including *Helicobacter pylori* associated stomach cancer (Matsumoto et al., 2007), again suggesting a link cytidine deamination and tumourigenesis (Okazaki et al., 2007). As the predominant mutation in cancer genomes is the C→T transition (Greenman et al., 2007, Sjoblom et al., 2006), irrespective of CpG, the present findings are consistent with the possibility that stochastic or transient over-expression of either of four human cytidine deaminase genes, notably AID, hA3A, hA3C and hA3H, might be sufficient to create an initial broad mutant spectrum from which the cancer genome eventually emerges.

The novel aspect of this work is the identification of the hA3A, hA3C and hA3H deaminases as powerful mutators of double stranded DNA. Mutation in a non-germinal, or somatic, cell is synonymous with the induction of cancer. However, as cancer has been described as a disease of the genome, it is considered that many mutations—estimates arrange from 20→80—are necessary to produce a fully developed cancer cell. Hence, aberrant expression of an APOBEC3 gene during the process that ends up in a full-blown cancer cell is also a possibility.

REFERENCES

M. Arbyn, J. Dillner, *J. Clin. Virol* 38, 189 (2007).
K. N. Bishop et al., *Curr. Biol.* 14, 1392 (2004).
H. P. Bogerd et al., *Proc. Natl. Acad. Sci. U.S.A.* 103, 8780 (2006).
V. Cogliano et al., *Lancet Oncol.* 6, 204 (2005).
S. G. Conticello, C. S. Thomas, S. K. Petersen-Mahrt, M. S. Neuberger, *Mol. Biol. Evol.* 22, 367 (2005).
Y. Dang, X. Wang, W. Esselman, Y. H. Zheng, *J. Virol.* 80, 10522 (2006).
E. M. de Villiers, C. Fauquet, Y. H. Broker, H. U. Bernard, H. zur Hausen, *Virology* 324, 17 (2004).
J. M. Di Noia, M. S. Neuberger, *Annu. Rev. Biochem.* 76, (2007).
M. F. Goodman, M. D. Scharff, F. E. Romesberg, *Adv. Immunol.* 94, 127 (2007).
C. Greenman et al., *Nature* 446, 153 (2007).
R. S. Harris et al., *Cell* 113, 803 (2003).
D. Lecossier, F. Bouchonnet, F. Clavel, A. J. Hance, *Science* 300, 1112 (2003).
P. Madsen et al., *Invest. Dermatol.* 113, 162 (1999).
Matsumoto Y, Marusawa H, Kinoshita K, Endo Y, Kou T, et al., Nat Med. 4, 470-6 (2007),
B. Mangeat et al., *Nature* 424, 99 (2003).
R. Mariani et al., *Cell* 114, 21 (2003).
M. OhAinle, J. A. Kerns, H. S. Malik, M. Emennan, *J. Virol.* 80, 3853 (2006).
I. M. Okazaki, A. Kotani, T. Honjo, *Adv. Immunol.* 94, 245 (2007).
Pham, Bransteitter, S. Petruska, M. F. Goodman, *Nature* 424, 103 (2003).
T. Sjoblom et al., *Science* 314, 268 (2006).
W. Stunkel, H. U. Bernard, *J. Virol.* 73, 1918 (1999).
R. Suspène et al., *Nucleic Acids Res.* 32, 2421 (2004).
R. Suspène, M. Henry, S. Guillot, S. Wain-Hobson, J.-P. Vartanian, *J. Gen. Virol.* 86, 125 (2005).
R. Suspène et al., *Proc. Natl. Acad. Sci. U.S.A.* 102, 8321 (2005).
N. R. Trivedi, K. L. Gilliland, W. Zhao, W. Liu, D. M. Thiboutot, J. *Invest, Dermatol.* 126, 1071 (2006).
H. L. Wiegand, B. P. Doehle, H. P. Bogerd, B. R. Cullen, *EMBO J.* 23, 2451 (2004).
H. Zhang et al., *Nature* 424, 94 (2003).

What is claimed:

1. A method for identifying a compound that increases hA3A, hA3C or hA3H activity in a cell comprising (i) contacting a cell expressing hA3A, hA3C or hA3H with a test compound and a substrate for hA3H, and measuring the level of cytidine deaminase activity, (ii) in a separate experiment, contacting a cell expressing hA3A, hA3C or hA3H and a substrate for hA3A, hA3C or hA3H in the absence of a test compound, and measuring the level of cytidine deaminase activity, where the conditions are essentially the same as in part (i) and then (iii) comparing the level of cytidine deaminase activity measured in part (i) with the level of cytidine deaminase activity in part (ii), wherein an increase level of cytidine deaminase activity in the presence of the compound indicates that the compound is a compound that increases hA3A, hA3C or hA3H activity in a cell.

2. The method of claim 1 wherein the substrate for hA3A, hA3C or hA3H is viral DNA.

3. The method of claim 2 wherein the viral DNA is human papilloma virus DNA.

4. The method of claim 2 wherein the level of cytidine deaminase activity is measured using a 3D-PCR assay.

* * * * *